United States Patent [19]

Strehlke et al.

[11] Patent Number: 5,021,434
[45] Date of Patent: Jun. 4, 1991

[54] N-SUBSTITUTED IMIDAZOLES, AS WELL AS THEIR USE IN PHARMACEUTICAL AGENTS

[75] Inventors: Peter Strehlke; Rolf Bohlmann; David Henderson, all of Berlin, Fed. Rep. of Germany

[73] Assignee: Schering Aktiengesellschaft, Berlin and Bergkamen, Fed. Rep. of Germany

[21] Appl. No.: 331,320

[22] Filed: Mar. 31, 1989

[30] Foreign Application Priority Data

Mar. 31, 1988 [DE] Fed. Rep. of Germany ....... 3811574

[51] Int. Cl.$^5$ ................ C07D 401/06; C07D 409/06; A61K 31/415
[52] U.S. Cl. .................................... 514/341; 514/397; 546/278; 548/336
[58] Field of Search ................ 548/336; 546/210, 278; 514/326, 397, 341, 396, 399

[56] References Cited

U.S. PATENT DOCUMENTS 4,416,895 11/1983 Thorogood .......................... 514/396

FOREIGN PATENT DOCUMENTS 1243298 10/1988 Canada .
0029742 6/1981 European Pat. Off. .
3228266 2/1984 Fed. Rep. of Germany .

OTHER PUBLICATIONS

*Chemical Abstracts*, 92: 58775x [Ger. Offen. 2,903,653, 8/2/79](1980).
*Chemical Abstracts*, 98: 160721m [Ger. Offen. 3,128,277, 2/3/83](1983).
*Chemical Abstracts*, 101: 23474a ]Ger. Offen. 3,228,266, 2/2/84](1984).

*Primary Examiner*—John M. Ford
*Attorney, Agent, or Firm*—Millen, White & Zelano

[57] ABSTRACT

The invention relates to N-substituted imidazoles, processes for their production as well as their use in pharmaceutical agents.

The compounds according to the invention have aromatase-inhibiting properties.

17 Claims, No Drawings

N-SUBSTITUTED IMIDAZOLES, AS WELL AS THEIR USE IN PHARMACEUTICAL AGENTS

SUMMARY OF THE INVENTION

The invention relates to N-substituted imidazoles, processes for their production as well as their use in pharmaceutical agents.

The compounds according to the invention are described by general formula I

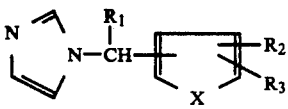

in which $R_1$ is a hydrogen atom, a saturated or unsaturated, straight-chain or branched-chain hydrocarbon radical with 1 to 10 carbon atoms or a cyclic hydrocarbon radical with 3 to 9 carbon atoms or a cycloalkylalkyl radical with 4 to 12 carbon atoms or an arylalkyl radical with 7 to 10 carbon atoms, $R_2$ is a hydrogen atom, a halogen atom, a cyano group, an optionally substituted methyl group, an optionally derivatized carboxyl group, an optionally substituted alkanoyl group with 2 to 10 carbon atoms, or an optionally substituted benzoyl group, $R_3$ is a hydrogen atom or an optionally substituted benzyloxy group and X is —CH=N—;

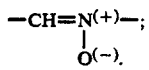

or S

The compounds can also be present in the form of their salts.

The saturated or unsaturated, straight-chain or branched-chain hydrocarbon radicals with 1 to 10 carbon atoms suitable as the radical $R_1$ are, for example, alkyl or alkenyl, e.g., the methyl, ethyl, propyl, propenyl, isopropyl, butyl, hexyl, octyl and decyl radicals. The propyl radical is preferred. Cyclic hydrocarbons include all those having 3 to 9 carbon atoms, e.g., the cyclopentyl and cyclohexyl radical can be mentioned, for example, cycloalkylalkyl radicals include all those having 4-12 carbon atoms, e.g., the cyclopentylmethyl and cyclohexylmethyl radical. Arylalkyl radicals include all those with 7 to 10 carbon atoms, e.g., the benzyl radical.

Fluorine, chlorine, bromine and iodine are suitable as the radical $R_2$ with bromine being preferred.

When $R_2$ is methyl, it may be substituted or unsubstituted. If substituted, suitable substituents include, for example, halogens (fluorine, chlorine, iodine or bromine), ether (e.g., $C_{1-6}$-alkoxy) or amine (e.g., mono- or di-$C_{1-4}$-alkyl-amino) radicals, hydroxyl, cyano and pyrrolidinyl radicals. Preferred substituents are hydroxyl, cyano, methoxy and pyrrolidinyl.

Further, $R_2$ has the meaning of an optionally derivatized carboxyl group, e.g., carboxylic acid $C_{1-6}$-alkyl esters and carboxylic acid amides, e.g., mono- or di-$C_{1-6}$-alkyl amides, anilides, or

Methyl, ethyl and butyl ester as well as acid amide, isopropylamide, anilide and pyrrolidinylamide are particularly preferred derivatives.

Further, $R_2$ has the meaning of an optionally substituted alkanoyl group with 2 to 10 carbon atoms. For example, this alkanoyl group can be straight-chain or branched-chain and can be substituted singly or repeatedly (e.g., 1–3) with the same or different substituents on any position of the chain. Acetyl, propanoyl, butyryl, valeryl and caproyl groups can be mentioned as preferred alkanoyl groups.

When the alkanoyl group is substituted, halogen atoms (e.g., fluorine, bromine, iodine and chlorine) as well as methoxy, ethoxy, amino, hydroxyl and cyano groups are suitable as substituents of the alkanoyl group.

$R_2$ may also be benzoyl, which may be substituted or unsubstituted. When substituted, the benzoyl group may be substituted 1-3 times in any position in the benzoyl group with the same or different substituents. Suitable substituents include, e.g., halogen atoms (fluorine, bromine, chlorine or iodine), $C_{1-4}$ alkyl, methoxy, ethoxy, amino, hydroxyl and cyano groups.

$R_3$ may be hydrogen or benzyloxy which may be substituted. When substituted, the benzyloxy group may be substituted 1-3 times with substituents which may be the same or different. Suitable substituents on the aromatic substance include, e.g., one or more halogen atoms (e.g., fluorine, chlorine, bromine and iodine), hydroxyl, ether, amino and cyano groups. 3-Bromo-, 4-bromo-, 4-chloro, 2,3-, 2,4-, 4,5- and 4,6-dichlorobenzyloxy groups are particularly preferred as substituted benzyloxy groups.

X may be —CH=N—;

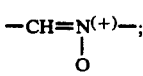

or S. These include divalent groups as radical X in which a pyridine, a pyridine-N-oxide or a thiophene ring are formed as aromatic substance.

The radicals $R_2$ and $R_3$ can be on all suitable positions of the aromatic ring.

As possible salts of the compounds of general formula I there can be mentioned physiologically compatible salts of organic or inorganic acids. The malonate, succinate, hydrochloride and hydrobromide are especially suitable as salts.

The compounds of general formula I are inhibitors of estrogen biosynthesis (aromatase inhibitors). Therefore they are suitable for treating diseases which are caused by estrogens or are dependent on estrogens. Thus they are suitable for treating estrogen-induced or estrogen-stimulated tumors, such as, for example, breast cancer or prostate hyperplasia (The Lancet, 1984. 1237-1239).

The compounds according to the invention are also valuable for affecting fertility. Thus, male infertility, which results from increased estrogen levels, can be eliminated with the new active ingredients.

Further, the compounds can be used in women in the reproductive age as a birth control agent to inhibit ovulation by estrogen deprivation.

The aromatase inhibitors are also suitable for treating imminent myocardial infarction, since increased estrogen levels can precede a myocardial infarction in males (see, e.g., U.S. Pat. No. 4,289,762).

Besides steroids, known substances exhibiting aromatase-inhibiting action are nonsteroidal substances; such as, for example, the various nitrogen heterocycles described in the European patent applications, publication numbers 0165777 to 0165784, the substituted glutaric acid imides described in J. Med. Chem. 1986, 29, pages 1362–1369, the substituted imidazobenzenes described in the European patent application, publication number 0165904 and the substituted heterocyclically substituted toluene nitriles described in the European patent application, publication number 0236940.

In comparison with other known nonsteroidal aromatase inhibitors the compounds of this application are distinguished in that they inhibit the enzyme system of the aromatase more strongly selectively without adversely affecting other enzyme systems in an appreciable manner.

Biological tests A and B are used to determine the enzymatic activities and enzyme selectivities of the compounds.

Test A

Determination of Aromatase Activity

The capabilities of compounds to inhibit the enzyme system of aromatase is tested on microsomes obtained from human placenta. The release of tritium-labeled water ($^3H_2O$), which is released as reaction product in the aromatizing of (1beta-$^3H$) androstrenedione to estrogen, is measured according to the method of Thompson and Siiteri (J. Biol. Chem. 249. 5364–72 (1974). The corresponding inhibition values ($K_1$, aromatase) are determined according to the method of Dixon (Biochem. J.94, 760 (1965) by graphic determination of the application of 1/v against the inhibition concentration.

Test B

Determination of 11-beta Hydroxylase Activity

The 11beta-hydroxylase activity is measured on mitochondria, obtained from bovine suprarenals. The reaction of [1,21-$^3H$]-17alpha-hydroxy-11-deoxycorticosterone in cortisol is determined by thin-film chromatography of the resulting reaction products according to a method of Mitani et al (J. Biol. Chem., 50, 8010–15 (1975). The concentration of the examined compound is determined, in which the reaction is inhibited by 50%, and the substrate concentration corresponds to the apparent $K_m$ value.

As an example of the aromatase inhibitors according to the invention, 5-[1-(1-imidazolyl)-butyl]-2-thienylpentyl-ketone (compound 2) and 3-(4-chlorobenzoyloxy)-4-[1-(1-imidazolyl)-pentyl-pyridine (compound 3) it is shown that in comparison with the aromatase inhibitor known in the literature 4-[1-(1-imidazolyl)-butyl]-benzonitrile (compound 1) (European patent application, publication No. 0 236 940), the compounds of this invention exhibit more selective effectiveness (test B) with similar (compound 2) and stronger inhibition action (compound 3) of aromatase than compound 1 (test A).

| Compound | Test A<br>$k_i$, aromatase | Test B<br>$IC_{50}$<br>11 beta-hydroxylase |
|---|---|---|
| Compound 1 | 1.1 nmol/L | 94 nmol/L |
| Compound 2 | 1.1 nmol/L | 1 micromol/L |
| Compound 3 | 0.64 nmol/L | 230 micromol/L |

The amount of the compounds to be administered varies within a wide range and can cover any effective amount. Depending on the condition to be treated and the kind of administration, the amount of compounds administered can be 0.0001–10 mg/kg of body weight, preferably 0.001–1 mg/kg of body weight, per day.

The dosage is 0.0001–10 mg/kg/day, preferably 0.001–1 mg/kg/day, analogous to the known agent aminoglutethimide when administered to treat estrogen-stimulated tumors, 0.0001–10 mg/kg/day, preferably 0.0001–1 mg/kg/day when administered analogous to the known agent aminoglutethimide to treat male infertility: 0.0001–10 mg/kg/day, preferably 0.0001–1 when administered analogously to the known agent 4-hydroxy-4-androstene-3,17-dione to inhibit ovulation, and 0.001–3 mg/kg/day, preferably 0.01–2 when administered analogously to the known agent 4-hydroxy-4-androstene-3,17-dione for the treatment of imminent myocardial infarction.

For the treatment of estrogen-stimulated tumors a dosage range of 0.005–0.05 mg/kg/day is mostly preferred.

Capsules, pills, tablets, dragees, etc. are suitable for oral application. Besides the active ingredient, the dosage units can contain a pharmaceutically compatible vehicle, such as, for example, starch, sugar, sorbitol, gelatin, lubricant, silicic acid, talc, etc. The individual dosage units for oral application can contain, for example, 0.05-50 mg of active ingredient (aromatase inhibitor).

For parenteral administration the active ingredients can be dissolved or suspended in a physiologically compatible diluent. Very often oils with or without addition of a solubilizer, a surfactant, a suspension or emulsion mixture is used as diluent. As examples for the oils used there can be mentioned: olive oil, peanut oil, cottonseed oil, soybean oil, castor oil and sesame oil.

The compounds can also be used in the form of a depot injection or an implant preparation, which can be formulated so that a delayed active ingredient release is made possible.

Implants can contain as inert materials, for example, biodegradable polymers or synthetic silicones, such as, for example, silicone rubber. Moreover, the active ingredients can be worked, for example, into plasters for percutaneous application.

Thus the invention also relates to pharmaceutical preparations and the use of the compounds for the production of these preparations for treatment of estrogen-caused diseases.

The invention further relates to processes for the production of substituted imidazoles of general formula I, characterized in that a) a compound of general formula II

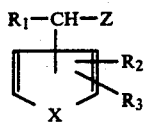  (II)

in which $R_1$, $R_2$, $R_3$ and X have the meaning mentioned in formula I, and Z means a leaving group, is reacted with a compound of general formula III

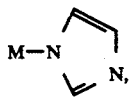  (III)

in which

M means a hydrogen atom or an alkali metal atom, or
b) a compound of general formula IV

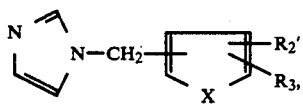  (IV)

in which $R_2$ has the same meaning as $R_2$ in formula I provided that $R_2$ is an electrophilic, nondeprotonatable radical, as well as $R_3$ and X have the meaning mentioned in formula I, is reacted, with a compound of general formula V $R_1$-Z  (V)

in which $R_1$ has the meaning mentioned in formula I; and
Z means a leaving group; or
c) a compound of general formula VI

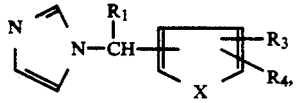  (VI)

in which $R_1$, $R_3$ and X have the meaning mentioned in formula I and $R_4$ means a halogen atom,
is reacted with a metal cyanide to form a cyano compound. The cyano compound can optionally be reacted with an organometallic compound to form an alkanoyl or optionally substituted benzoyl derivative; or the cyano compound can be hydrolytically reacted to form a carboxyl compound or carboxylic acid amide. The carboxyl compound formed can be further reacted with an alcohol to form a ester. The ester can be reacted with a reducing agent to form a hydroxymethyl compound. Optionally, the hydroxymethyl compound is reacted with a halogenating agent to form a halomethyl compound. The halomethyl compound can optionally be reacted with cyanide to form a cyanomethyl compound. Alternatively, the carboxyl compound can be reacted with a halogenating agent to form a carboxylic acid halide which can optionally be reacted with ammonia to form a carboxylic acid amide or with amines to form a substituted carboxylic acid amides;

d) a compound of general formula VII

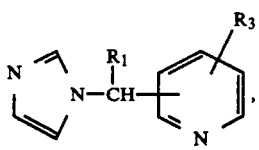  (VII)

in which $R_1$ and $R_3$ have the meaning mentioned in formula I, is reacted with an oxidizing agent to the pyridine-N-oxide and optionally with an electrophile and a metal cyanide or with trimethylsilyl cyanide to form a cyano compound.

Easily substitutable groups, known from the literature, are suitable as leaving groups Z for the reactions mentioned under a). As such functional groups suitable for leaving group capability can be mentioned, for example, the benzylic, hydroxyl, mesyl, tosyl, triflat and acetyl group. Also the halogens, e.g., chlorine and bromine, are also suitable groups. The methods to be used are described, among others, in Eur. J. Med. Chem. 1979, pages 231-237.

Hydrogen and alkali metal atoms are suitable as substituents M of general formula III. Lithium, sodium and potassium are preferred as alkali metal atoms.

The reactions, which are listed under a), the reactions of compounds of general formula II with compounds of general formula III, can be performed in all inert organic solvents. For example, dimethylformamide, dimethyl sulfoxide and various ethers (e.g., tetrahydrofuran, dioxane and diethyl ether) are suitable as solvents. The reaction of the compounds of formula II with imidazole (formula III, M=H) can also be performed without a solvent and at temperatures between the melting point and the boiling point of the imidazole, preferably between 100° C. and 200° C.

The production of the compounds of general formula I can also be performed according to process b). In this case, reaction of compounds of general formula IV with compounds of general formula V takes place. All usual leaving groups, e.g., those named in a), are suitable as leaving group Z of the compounds of general formula V.

For the production of the compound of general formula I according to process b) the corresponding benzyl anion is produced with bases from the compounds of general formula IV and reacted by standard methods with the compounds of general formula V. The benzyl -CH2-group in the compounds of general formula IV can be deprotonated by means of bases, for example by reaction with tertiary amines, sodium hydride, lithium hydride or lithium diisopropylamide and magnesium hydride, and be reacted with compounds of general formula V. Process b) is preferably used if $R_2$ represents an acceptor group, for example a cyano or a benzoyl group.

The reaction may be carried out with or without a solvent at a temperature of −100° to +100° C. When a solvent is used, suitable solvents include inert solvents, such as ethers, e.g., tetrahydrofuran, dioxane and diethylether or dimethylformamide, etc.

The compounds of general formula I according to the invention can be produced according to process c). In this case, compounds of general formula VI are reacted according to standard methods. Halogen atoms, for example chlorine and bromine, are suitable as possible radicals R4.

The halogen compounds can be converted into the corresponding cyano compounds by nucleophilic substitution of a metal cyanide, for example, copper(I) cyanide.

The resulting cyano compounds can further be converted, with organometallic compounds, for example, Grignard compounds, into the alkanoyl or benzoyl compounds. If the cyano compounds are reduced with special reducing agents, such as sodium triethoxyaluminum hydride, lithium triethoxyaluminium hydride, sodium aluminum hydride or aluminum-nickel alloys in acids, preferably formic acid, the corresponding aldehydes are obtained. The cyano compounds can converted under hydrolytic conditions into the corresponding carboxylic acids or carboxylic acid amides. The resulting carboxyl compounds can optionally be reacted with alcohols under standard conditions of esterification into the corresponding carboxylic acid esters.

The carboxylic acid esters can in turn be initial products for a series of secondary products. Thus, the esters can be converted, with reducing agents, for example lithium aluminum hydride, into the hydroxymethyl derivatives.

The hydroxymethyl derivatives can be reacted with halogenating agents, for example, thionyl chloride, into the halomethyl derivatives, for example into the chloromethyl derivatives. The halomethyl compounds, by nucleophilic substitution, for example by reaction with alkali cyanide, ammonia or amines, can further be converted into the cyanomethyl, aminomethyl or alkylaminomethyl compounds.

The resulting carboxyl compounds can be converted, with halogenating agents, for example thionyl chloride, into the acid halides, for example acid chlorides. The carboxylic acid halides in turn are initial material for a series of secondary products. The corresponding amides can be obtained by reaction with ammonia or amines.

Compounds of general formula I, in which X means —CH=N or —CH=NO, can also be produced according to process d). In this case, compounds of general formula VII are converted, with an oxidizing agent, for example hydrogen peroxide, into the corresponding pyridine-N-oxides. If these pyridine-N-oxides are reacted according to the methods described in Heterocycles 22 (1984), p. 2375, the compounds of general formula I are obtained, in which $R_2$ stands for a cyano group. The cyano compounds can be converted, as described under process c) into secondary products.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application West German P 38 11 574.3, filed Mar. 31, 1988, are hereby incorporated by reference.

EXAMPLES

EXAMPLE 1

2-[1-(I-Imidazolyl)-butyl]-5-bromo-thiophene

Starting 5-bromo-thiophene-2-carbaldehyde, by reaction with propyl magnesium bromide, a secondary alcohol is obtained, which in turn can be converted, by reaction with thionyl chloride, into the 1-(5-bromo-2-thienyl)-I-chloropropane. 0.122 g of imidazole is dissolved in 3 ml of dimethylformamide and mixed with 0.054 g of (80%) sodium hydride. It is stirred for 1 hour at room temperature. 0.360 g of 1-(5-bromo-2-thienyl)-1-chloropropane in 2 ml of dimethylformamide is instilled in this solution and stirred overnight at room temperature. Then the reaction mixture is poured into 100 ml of 2 n hydrochloric acid and extracted with ether. The aqueous phase is made alkaline with potassium carbonate and then extracted with ethyl acetate. The ethyl acetate phase is concentrated by evaporation in a vacuum and the residue is distilled on a bulb tube.

Boiling point: 180°–200° C./0.03 mbar. 0.70 g of 2-[1-(1-imidazolyl)-butyl]-5-bromo-thiophene is obtained.

EXAMPLE 2

5-[1-(1-imidazolyl)-butyl]-thiophene-2-carbonitrile 0.04 g of bromine compound (of example 1) is dissolved in 2 ml of N- methylpyrrolidine, 0.05 g of copper(I) cyanide is added and stirred under argon for 5 hours at 180° C. Ammonia water is added to the reaction solution and then extracted with ethyl acetate. The organic phase is concentrated by evaporation in a vacuum and the remaining oil is distilled on a bulb tube, boiling point 180° C./0.03 mbar. 0.01 g of 5-[1-(1-imidazolyl)-butyl]thiophene-2-carbonitrile is obtained.

EXAMPLE 3

2-[1-(1-Imidazolyl)-butyl]-4-bromo-thiophene 1-(4-Bromo-2-thienyl)-I-chlorobutane is obtained from commercial 4-bromo-thiophene-2-carbaldehyde by reaction with propylmagnesium bromide and then chlorination thionyl chloride. The reaction of the chlorine compound with imidazole takes place analogously to example 12-[1-(1-Imidazolyl)-butyl]-4-bromothiophene is obtained.

EXAMPLE 4

2-[1-(1-Imidazolyl)-butyl]-thiophene-4-carbonitrile 0.3 g of 2-[1-(1-imidazolyl)-butyl]-4-bromothiophene is dissolved in 5 ml of N-methylpyrrolidine and mixed with 0.3 g of copper(I) cyanide and stirred for 5 hours at 180° C. Then the reaction mixture is poured into 100 ml of dilute ammonia solution and extracted with ethyl acetate. The ethyl acetate phase is concentrated by evaporation in a vacuum and distilled on a bulb tube, boiling point 180° C./0.03 mbar. 0.190 g of 2-[1-(1-imidazolyl)-butyl]-thiophene-4-carbonitrile is obtained.

EXAMPLE 5

5-[1-(I-Imidazolyl)-butyl]-2-thienyl-pentyl-ketone

A solution of 0.69 g of cyano compound of example 2 in 3 ml of tetrahydrofuran and 0.015 g of copper(I) bromide is added to a Grignard solution prepared from 0.182 g of magnesium and 0.93 ml of pentylbromide in 2 ml of tetrahydrofuran. After stirring for 20 hours at room temperature, it is added to 2 M hydrochloric acid and extracted with ether. The aqueous phase is alkalized with potassium carbonate, extracted with ethyl acetate, dried, concentrated by evaporation and the residue is distilled on a bulb tube. 0.3 g of the title compound is obtained at yellow oil, boiling point: 200°–230° C./0.03 mbar.

EXAMPLE 6

5-[1-(1-Imidazolyl)-butyl]-2-thiophene-carboxylic acid, hydrochloride 1 g of cyano compound of example 2 is refluxed with 5 ml of concentrated hydrochloric acid for 3 hours. After concentration by evaporation in a vacuum, it is redistilled three times with toluene and the residue is boiled with isopropanol. The title compound is obtained as a viscous yellow resin.

EXAMPLE 7

5-[1-(1-imidazolyl)-butyl]-2-thiophene-carboxylic acid butyl ester 1.2 g of the acid of example 6 is dissolved in 20 ml of butanol and the solution is saturated with hydrochloric-acid gas under ice cooling. After 20 hours, it is concentrated by evaporation, distributed between potassium carbonate solution and ether and the ether phase is separated. After drying and concentration by evaporation of the solvent, it is distilled on the bulb tube. 200 mg of the title compound is obtained. Boiling point: 230° C./0.03 mbar.

EXAMPLE 8

5-[1-(1-Imidazolyl)-butyl]-thiophene-2-methanol 0.2 g of the butyl ester of example 7 is reduced in 3 ml of tetrahydrofuran with 0.2 g of lithium aluminum hydride and worked up in the usual way. 0.2 g of the title compound is obtained as oil.

EXAMPLE 9

5-[1-(1-Imidazolyl)-butyl]-thiophene-2-acetonitrile 0.2 g of the alcohol of example 8 is converted, with thionyl chloride (2 hours at room temperature, concentration by evaporation, redistillation three times with toluene) into the hydrochloride of the chloromethyl compound, which is dissolved in 2 ml of dimethyl sulfoxide and is mixed with 0.2 g of sodium cyanide. After stirring for 20 hours, it is added to dilute ammonia solution, extracted with ethyl acetate and the ethyl acetate extract is dried and concentrated by evaporation. After distillation on a bulb tube, the title compound is obtained as oil. Boiling point: 210°–230° C./0.03 mbar.

EXAMPLE 10

5-[1-(1-Imidazolyl)-butyl]-2-thiophene carboxylic acid anilide 0.7 g of the acid of example 6 is converted in the usual way with thionyl chloride into the acid chloride and is converted with 0.91 ml of aniline in 10 ml of methylene chloride into the amide. After recrystallization from toluene, 0.18 g of the title compound with a melting point of 165°–166° C. is obtained.

EXAMPLE 11

1-(Cyclohexyl-2-thienyl-methyl)-imidazole

2-Thienyl lithium is produced in 100 ml of ether in the usual way from 12.6 g of thiophene and 94 ml of a 1.6 molar solution of butyllithium in hexane and reacted with 16.8 g of cyclohexanealdehyde at −40° C. After 15 minutes at −40° C. and an hour at room temperature it is worked up in the usual way and distilled; 14 g of cyclohexyl-(2-thienyl)-methanol is obtained, boiling point: 166°–172° C./20 mbar.

0.5 g of it is dissolved in 10 ml of methylene chloride with 1 ml of thionyl chloride under ice cooling; after 20 minutes at room temperature, it is concentrated by evaporation in a vacuum and redistilled with toluene. The chloride is warmed with 0.55 g of imidazole for 20 hours at 160° C. Then it is distributed between excess 2 M hydrochloric acid and ether, the aqueous phase is alkalized with potassium carbonate and extracted with ethyl acetate. After drying and concentration by evaporation, it is distilled on a bulb tube. The title compound is obtained as an oil with a boiling point of 230° C./0.03 mbar. By trituration with ether, the compound crystallizes; melting point 90°–92° C.

EXAMPLE 12

{5-[1-(1-Imidazolyl)-butyl)-2-thienyl]}-ethyl-ketone

Analogously to example 5, the cyano compound is reacted with ethyl magnesium bromide. The title compound boils on a bulb tube at 220° C./0.03 mbar.

EXAMPLE 13

4-[1-(1-Imidazolyl)-butyl]-pyridine

The initial material, 4-(1-chlorobutyl)-pyridine, necessary for this reaction is obtained by the following reaction sequence. Commercial 4-bromo-pyridine is converted, by halometal exchange, into the corresponding 4-lithium-pyridine compound. This lithium compound is converted, with butyraldehyde, into the corresponding secondary alcohol. The alcohol is then converted by reaction with thionyl chloride into 4-(1-chlorobutyl)pyridine. 0.68 g of imidazole is dissolved in 5 ml of dimethylformamide, 0.3 g of sodium hydride (80%) is added and stirred for 10 minutes at room temperature. A solution of 3.87 g of 4-(1-chlorobutyl)-pyridine in 4 ml of dimethylformamide is added to this solution and stirred for 24 hours at room temperature. Then it is poured into 100 ml of 10% hydrochloric acid and extracted with ethyl acetate. The aqueous phase is made alkaline with sodium hydroxide solution (pH 13) and extracted with methylene chloride. The methylene chloride solution is concentrated by evaporation in a vacuum and the residue is distilled on a bulb tube, boiling point: 170°–190° C./0.04 mbar. 0.3 g of 4-[1-(1-imidazolyl)-butyl]-pyridine is obtained.

EXAMPLE 14

3-[1-(1-Imidazolyl)-butyl]-pyridine

The production of this derivative takes place analogously to example 13. Starting from 3-bromopyridine, the corresponding 3-lithium pyridine compound is produced and reacted with butyraldehyde. The secondary alcohol is converted by reaction with thionyl chloride into the chlorine compound. By substitution of the chlorine by imidazole, 3-[1-(1-imidazolyl)-butyl]-pyridine is obtained. The compound boils between 180° and 190° C./0.03 mbar.

EXAMPLE 15

3-[1-(1-Imidazolyl)-butyl]-pyridine-N-oxide 1.0 g of 4-[1-(1-imidazolyl)-butyl]-pyridine (example 13) is put into 10 ml of methylene chloride. A solution consisting of 2.1 g of m-chloroperbenzoic acid, dissolved in 10 ml of methylene chloride, is instilled in it. It is stirred for 20 hours at room temperature. Then 5 ml of 3 N hydrochloric acid is added, it is extracted 3 times with ether, the aqueous phase is concentrated by evaporation in a vacuum. 1.4 g of a light yellow resin is obtained. This resin is dissolved in 10 ml of methanol and added by a basic ion exchanger (ion exchanger III of the Merck Co.). The methanolic solution is then concentrated by evaporation. 0.8 g of 4-[1-(1-imidazolyl)-butyl]-pyridine-N-oxide is obtained.

EXAMPLE 16

3-[1-(1-Imidazolyl)-butyl]-pyridine-N-oxide

Analogously to the reaction indicated under example 15, the 3-[1-(1-imidazolyl)-butyl]-pyridine is reacted with m-chloroperbenzoic acid to the 3-[1-(1-imidazolyl)-butyl]-pyridine-N-oxide.

EXAMPLE 17

4-[1-(1-Imidazolyl)-butyl]-2-cyanopyridine 0.109 g of 4-[1-(1-imidazolyl)-butyl]pyridine-N-oxide is dissolved in 2 ml of acetonitrile, 0.150 g of trimethylsilyl cyanide and 0.101 g of triethylamine are added to it. The reaction is left for 22 hours at 110° C. The mixture is concentrated by evaporation in a vacuum and then distilled on a bulb tube, boiling point: 210°–220° C./0.035 mbar. 0.102 g of 4-[1-(1-imidazolyl)-butyl]-2-cyanopyridine is obtained as brownish oil.

EXAMPLE 18

Mixture consisting of
3-[1-(1-imidazolyl)-butyl]-6-cyanopyridine and
3-[1-(1-imidazolyl)-butyl]-2-cyanopyridine 0.6 g of 3-[1-(I-imidazolyl)-butyl]-pyridine-N-oxide (example 16) is dissolved in 6 ml of acetonitrile, 0.63 ml of triethylamine and 1.0 ml of trimethylsilyl cyanide are added to it. It is stirred for 24 hours at 100° C. Working up takes place analogously to example 17. After bulb tube distillation, 0.6 of a brown oil is obtained, boiling point: 210°–240° C./0.03 mbar. It is established by NMR analysis that a mixture of 3-[1-(1-imidazolyl)-butyl]-6-cyanopyridine and 3-[1-(1-imidazolyl)-butyl]-2-cyanopyridine is present.

EXAMPLE 19

3-(4-chlorobenzyloxy)-4-[1-(1-imidazolyl)-pentyl]-pyridine

Starting from 3-chloro-4-pyridine carbonitrile, by reaction with 4-chlorobenzyl alcohol in the presence of sodium hydride in dimethylformamide, 3-(4-chlorobenzyloxy)-4-pyridine carbonitrile is obtained, which is reacted with butyllithium in diethyl ether to 3-(4-chlorobenzyloxy)-4-valeryl pyridine. The keto group of this 4-valeryl derivative is reduced with sodium boron hydride to the hydroxyl group; 1-[3-(4-chlorobenzyloxy)-4-pyridyl]-1-pentanol is obtained. The hydroxyl group of the pentanol derivative is exchanged with thionyl chloride in methylene chloride for a chlorine group, 3-(4-chlorobenzyloxy)-4-(1-chloropentyl)-pyridine is obtained. By subsequent reaction with imidazole in the presence of sodium hydride (analogously to example 13), the 3-(4-chlorobenzyloxy)-4-[1-(1-imidazolyl)-pentyl]-pyridine is obtained.

EXAMPLE 20

3-(4-chlorobenzyloxy)-4-[1-(1-imidazolyl)-pentyl]-pyridine-N-oxide 0.624 g of 3-(4-chlorobenzyloxy)-4-[1-(1-imidazolyl)-pentyl]-pyridine is reacted analogously to example 15 with 0.410 g of m-chloroperbenzoic acid to the title compound.

EXAMPLE 21

Mixture consisting of
5-(4-chlorobenzyloxy)-4-[1-(1-imidazolyl)-pentyl]-pyridine-2-carbonitrile and
3-(4-chlorobenzoyloxy)-4-[1-(1-imidazolyl)-pentyl]-pyridine-2-carbonitrile.

0.578 g of 3-(4-chlorobenzyloxy)-4-[1-(1-imidazolyl)-pentyl]-pyridine-N-oxide is reacted with 0.450 g of trimethylsilyl cyanide according to example 18. 0.483 g of a mixture consisting of the title compounds is obtained. The compounds can be separated by high-pressure liquid chromatography, system methylene chloride/methanol (9:1). 5-(4-Chlorobenzyloxy)-4-[1-(1-imidazolyl)-pentyl]-pyridine-2-carbonitrile melts at 132°–134° C., 3-(4-chlorobenzyloxy)-4-[1-(1-imidazolyl)-pentyl]-pyridine-2-carbonitrile is a brownish oil.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazole of the formula

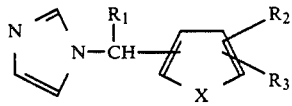

wherein
$R_1$ is $C_{1-10}$-alkyl, $C_{2-10}$-alkenyl, $C_{3-9}$-cycloalkyl, $C_{3-9}$-cycloalkenyl, $C_{4-12}$-cycloalkylalkyl or $C_{7-10}$-arylalkyl;
$R_2$ is hydrogen; halogen; a cyano group, a methyl group; methyl substituted with halogen, cyano, hydroxy, $C_{1-4}$-alkoxy, mono- or di-$C_{1-16}$-alkylamine, or pyrrolidonyl; a carboxyl group or a $C_{1-6}$-alkyl ester, amide, $C_{1-16}$-alkyl amide, anilide or $N(CH_2)_{4-5}$ derivative thereof; an alkanoyl group with 2 to 10 carbon atoms; an alkanoyl having 2 to 10 carbon atoms substituted with halogen, methoxy, ethoxy, amino, hydroxyl, cyano or a combination thereof; a benzoyl group, or a benzoyl group substituted with halogen, $C_{1-4}$-alkyl, methoxy, ethoxy, amino, hydroxy, cyano or a combination thereof;
$R_3$ is a hydrogen atom, a benzyloxy group, or benzyloxy substituted with halogen, hydroxyl, ether, amino, cyano or combinations thereof;
X means -CH=N;

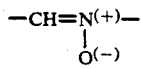

or S or a pharmaceutically acceptable salt thereof.

2. A compound according to claim 1
5-[1-(1-imidazolyl)-butyl]-thiophene-2-carbonitrile;
2-[1-(1-imidazolyl)-butyl]-thiophene-4-carbonitrile;
2-[1-(1-imidazolyl)-butyl]-4-bromo-thiophene;
2-[1-(1-imidazolyl)-butyl]-5-bromo-thiophene;
{5-[1-(1-imidazolyl)-butyl]-2-thienyl}-pentyl-ketone;
{5-[1-(1-imidazolyl)-butyl]-2-thienyl}-ethyl-ketone;
5-[1-(1-imidazolyl)-butyl]-2-thiophene-carboxylic acid, hydrochloride;
5-[1-(1-imidazolyl)-butyl]-2-thiophene-carboxylic acid butyl ester;
5-[1-(1-imidazolyl)-butyl]-2-thiophene-carboxylic acid ethyl ester;
5-[1-(1-imidazolyl)-butyl]-thiophene-2-methanol;
5-[1-(1-imidazolyl)-butyl]-thiophene-2-acetonitrile;
5-[1-(1-imidazolyl)-butyl]-thiophene-2-carboxylic acid anilide;
1-(cyclohexyl-2-thienyl-methyl)-imidazole;
4-[1-(1-imidazolyl)-butyl]-pyridine;
4-[1-(1-imidazolyl)-butyl]-pyridine-N-oxide;
4-[1-(1-imidazolyl)-butyl]-2-cyanopyridine;
3-[1-(1-imidazolyl)-butyl]-pyridine;
3-[1-(1-imidazolyl)-butyl]-pyridine-N-oxide;
3-[1-(1-imidazolyl)-butyl]-6-cyanopyridine;
3-[1-(1-imidazolyl)-butyl]-2-cyanopyridine;
5-(4-chlorobenzyloxy)-4-[1-(1-imidazolyl)-pentyl]-pyridine-2-carbonitrile;
3-(4-chlorobenzyloxy)-4-[1-(1-imidazolyl)-pentyl]-pyridine-2-carbonitrile;
3-(4-chlorobenzyloxy)-4-[1-(1-imidazolyl)-pentyl]-pyridine-N-oxide; or 3-(4-chlorobenzyloxy)-4-[1-(1-imidazolyl)-pentyl-pyridine.

3. A pharmaceutical composition comprising an effective amount of a compound of claim 1 and a pharmaceutically acceptable carrier.

4. A pharmaceutical composition comprising an effective amount of a compound of claim 2 and a pharmaceutically acceptable carrier.

5. A method of treating estrogen-stimulated tumors in a patient in need of such treatment, comprising administering an effective amount of a compound of claim 1.

6. A method according to claim 5, wherein the effective amount is 0.0001-10 mg/kg/day.

7. A method of ameliorating male infertility in a host comprising an effective amount of a compound of claim 1.

8. A method according to claim 5, wherein the effective amount is 0.0001-10 mg/kg/day.

9. A method of inhibiting ovulation comprising administering to a female otherwise capable of ovulation an effective amount of a compound of claim 1.

10. A method according to claim 9, wherein the effective amount is 0.0001-10 mg/kg/day.

11. A method of treating imminent myocardial infarction in a patient in need of such treatment, comprising administering an effective amount of a compound of claim 1.

12. A method according to claim 11, wherein the effective amount is 0.0001-10 mg/kg/day.

13. A compound of claim 1, wherein $R_1$ is methyl, ethyl, propyl, propenyl, isopropyl, butyl, hexyl, octyl, decyl, cyclopentyl, cyclohexyl, cyclopentylmethyl, cyclohexylmethyl or benzyl.

14. A compound of claim 1, wherein $R_2$ is bromine, methyl substituted with hydroxyl, cyano, methoxy or pyrrolidinyl; a methyl carboxylic acid ester; an ethyl carboxylic ester; a butyl carboxylic acid ester; a carboxylic acid amide; a carboxylic acid isopropyl amide; a carboxylic acid anilide or a carboxylic acid pyrrolidinyl amide.

15. A compound of claim 1, wherein $R_2$ is benzoyl, benzoyl substituted with $C_{1-4}$-alkyl, methoxy, ethoxy, amino, hydroxyl, cyano.

16. A compound of claim 1, wherein $R_3$ is 3-bromobenzyloxy, 4-bromobenzyloxy, 4-chlorobenzyloxy, 4-chlorobenzyloxy, 2,3-dichlorobenzyloxy, 2,4-dichlorobenzyloxy, 4,5-dichlorobenzyloxy or 4,6-dichlorobenzyloxy.

17. A method of treating estrogen-stimulated tumors, ameliorating male infertility, inhibiting ovulation and/or treating imminent myocardial infarction comprising administering an effective amount of a compound of claim 2.

* * * * *